United States Patent [19]

McCorkle

[11] 3,965,747

[45] June 29, 1976

[54] GAS SAMPLING SYSTEM AND METHOD
[75] Inventor: Richard E. McCorkle, Glendale, Calif.
[73] Assignee: Joy Manufacturing Company, Pittsburgh, Pa.
[22] Filed: Oct. 24, 1972
[21] Appl. No.: 300,001

[52] U.S. Cl................................................ 73/421.5 R
[51] Int. Cl.²........................................................ G01N 1/24
[58] Field of Search............... 73/421.5 R, 421.5 A, 73/299, 23; 23/254, 256

[56] References Cited
UNITED STATES PATENTS

| | | | |
|---|---|---|---|
| 2,982,131 | 5/1961 | Rosinski | 73/421.5 R |
| 3,384,457 | 5/1968 | Norell | 73/421.5 R |
| 3,433,067 | 3/1969 | St. Clair | 73/199 |

Primary Examiner—S. Clement Swisher

[57] ABSTRACT

A gas sampling system and method which employ a vacuum pressure regulator in a gas sampling train to simplify isokinetic sampling at selected locations of a sampling nozzle in a gas conducting flue.

9 Claims, 2 Drawing Figures

GAS SAMPLING SYSTEM AND METHOD

In order to determine the performance of a gas handling or gas cleaning system or to evaluate the necessity of installing a cleaning system to treat a gas stream, and the like, it is necessary to obtain a measure of concentration and character of the dust in the gas stream and accurate data regarding the temperature, velocity and volume rate of flow of the gas stream itself.

In making such a determination it is often necessary to accurately sample the gas flowing through a gas conducting flue by the use of a gas sampling nozzle positionable at selected locations within the flue wherein the gas is flowing. It is well known by those familiar with the field of gas handling and cleaning operations that for best results sampling should be done isokinetically, that is, the flow of gas through the nozzle should be as nearly as possible the same velocity as the flow of gas through the flue in the sampling location.

In a typical test situation a vacuum source is utilized to move contaminated gas through the sampling nozzle and filter assembly, through a condenser and finally through a dry gas meter. In this arrangement any variation in the rate of gas stream flow will cause a change in the absolute pressure in the dry gas meter which in turn requires calculations to determine the true gas volume. By providing a vacuum regulator between the vacuum source and the dry gas meter the pressure in the meter is caused to remain constant with the result that calculation of the actual volume measured by the gas meter is simplified because the originally variable pressure in the gas meter is now a constant value.

Thus, the advantages resident in the apparatus of this invention include simplified calculations, more rapid calculations, and less likelihood of error.

These and other advantages and objects of this invention will become more readily apparent upon consideration of the following description and drawings wherein.

Figure 1:
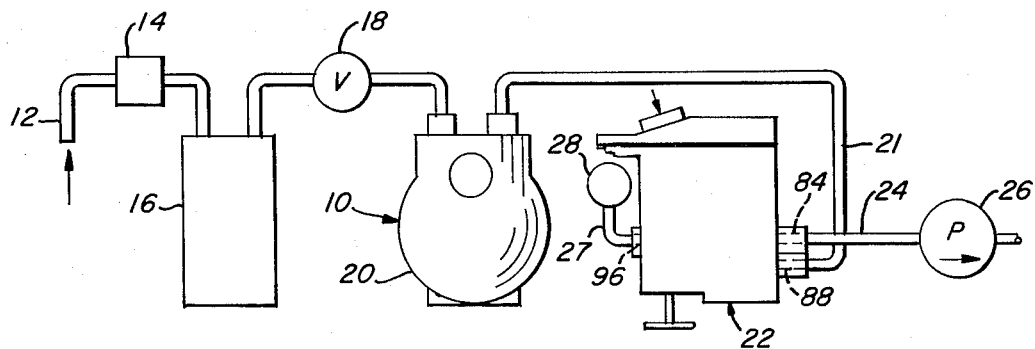
FIG. 1 is a schematic representation of the gas sampling apparatus of this invention.

In FIG. 1 there is seen a gas sampling apparatus generally indicated at 10 constructed according to the principles of this invention and comprising a gas sampling nozzle 12 to be inserted and mounted in a flue at a preselected location but maintained in direct communication with a sampling filter 14 of a size and type suited to the suspensoid concentration upon which a determination is being run.

Immediately down stream from and communicating with the filter 14 is a condenser 16 of a well known type for removing any condensed liquid from the sample stream so that the gas may be measured in a dry condition. Downstream from the condenser 16 is installed a control valve 18 adjustable in a variety of throttling positions to provide the desired volume rate of flow as measured by a dry gas meter 20 of a well known type which will measure the volume of gas passing therethrough.

Downstream from the gas meter 20 and communicating therewith by way of gas conducting means such as tubing 21 is a vacuum pressure regulator generally indicated at 22 and more completely described hereinbelow. A second gas conducting means communicating with the regulator 22 is indicated as tubing 24 communicating with a gas moving means of any suitable type such as a vacuum pump 26 suitably energized and of a size to provide more gas flow than is necessary for the nozzle 12 to be operating isokinetically.

Figure 2:
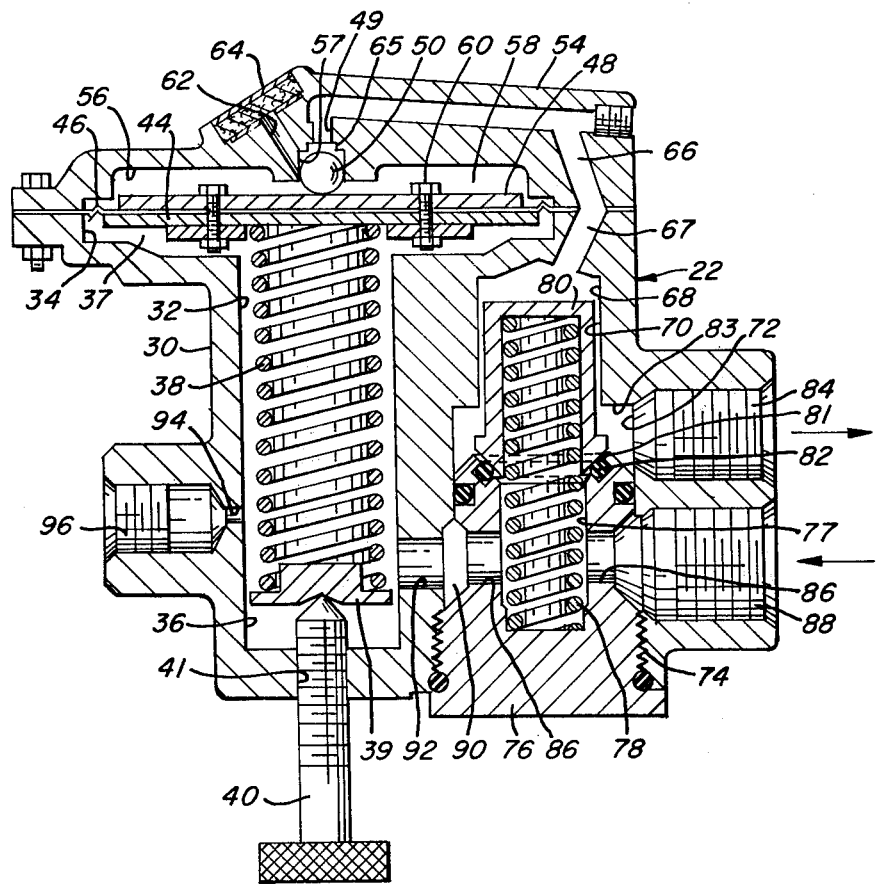
FIG. 2 is an enlarged sectional view of a vacuum regulator such as that shown in FIG. 1.

In FIG. 2 there is shown a sectional partially schematic view of the regulator 22 comprising a generally rectangular hollow body 30 having an upwardly open stepped cylindrical opening 32 extending from a large diameter upper portion 34 downwardly, in a smaller diameter portion 36 through a major portion of the body 30. Portion 36 is suitably sized to receive and retain in vertical position an elongated compression type spring 38 mounted upon and extending upwardly from a spring retainer 39 adjustably supported by an adjusting screw 40 threadedly engaged in a threaded bore 41 coaxial with the stepped cylindrical opening 32 and extending through the outer portion of the body 30.

The top end of the spring 38 is engaged with a horizontally extending diaphragm supporting plate 44 engaged with the underside of an impermeable flexible horizontal diaphragm 46 extending completely across the top surface of the body 30 to enclose the opening 32 within the body 30 and form a chamber 37.

On the upper side of the diaphragm 46 there is a wide flat plate 48 which provides support for a ball type valve 50. Rigidly secured to and covering the entire top surface of the body 30 is a cap element 54 provided with a downwardly open recess 56 extending over and mating with the large diameter portion 34 of the opening 32 to form a chamber 58 separated from the chamber 37 by the diaphragm 46. The opening 56 is continued in a central, upwardly extending shouldered bore 49 of the cap element 54 and has a bore portion 57 suitably sized to receive and guide the ball valve 50 upwardly movable in the bore portion 57 to contact a valve seat 65. The plate 48 is secured to the top of the diaphragm 46 and the plate 44 by suitable fasteners such as bolts 60 extending through the plate 48 and through the plate 44 to provide a clamping stiffener for the diaphragm central portion in a well-known manner. The portion 57 of the bore 49 communicates with the surrounding atmosphere by way of a stepped bore 62 having mounted in an outer larger diameter portion a a filter 64 to prevent entrance of any dust or other foreign matter into the chamber 58 when conditions hereinafter described cause air from the surrounding atmosphere to enter the chamber 58.

A suitable air conducting passageway 66 formed in the cap element 54 extends generally horizontally from the valve seat 65 in the portion 57 of the bore 49 and downwardly through an opening in the diaphragm 46 into communication with a passageway 67 formed in the upper portion of body 30 and leading to a stepped cylindrical downwardly open chamber 68 in the body 30. Chamber 68 has a relatively small diameter cylindrical upper portion 70 an intermediate diameter central portion 72 with a relatively large diameter partially threaded lower portion 74 extending upwardly and inwardly from the outer surface of the body 30 to the central portion 72. Within the lower portion 74 of the chamber 68, there is threadedly and sealingly received a plug member 76 extending upwardly within the portion 74 and having a cup-shaped hollow upper portion sealingly received within the intermediate bore portion 72 with cup-shaped central opening 77 of the hollow plug 76 in open communication with bore portion 72 and suitably sized to receive and support an elongated upwardly extending, compression type spring 78.

Internally receiving the spring 78, mounted upon and biased upwardly by the spring 78, is a downwardly open, inverted cup-shaped poppet element 80 slidably received within the small diameter upper portion 70 of chamber 68. Poppet element 80 is provided around its lower extremity with a conical sealing surface 81 to provide sealing engagement with an "O" ring mounted in the upper end of the hollow plug element 76 for a purpose to be described. The intermediate portion 72 of the chamber 68 communicates by way of a horizontal bore 83 with a threaded port 84 which in turn receives and communicates with the tubing 24 above described (see FIG. 1). The opening 77 communicates by way of a series of horizontal bores 86 with a circumferential passageway 90 formed between a reduced diameter portion of the plug member 76 and the upper part of the lower bore portion 74. Passageway 90 in turn communicates with a port 88 threaded to suitably receive the tubing 21 of the FIG. 1 description.

The passageway 90 also communicates between the plug opening 77 and a passageway 92 which in turn communicates with the lower portion 36 of the opening 32 earlier described. Similarly a horizontal passageway 94 communicates between the opposite side of the small diameter portion 36 of the opening 32 and a port 96 threadedly sealingly receiving a suitable tubing 27 leading to a pressure gage 28 (see FIG. 1) for a purpose to be described.

Operation of the regulator 22 begins with all chambers and passageways at atmospheric pressure and vacuum pump 26 just being started. Under these conditions the poppet 80 will be in its uppermost position with open communication between tubing 24 and tubing 21 through port 84, bore 83, intermediate portion 72 of chamber 68, plug opening 77, bore 86, passageway 90 and port 88 so that air being removed from tubing 24 by the pump 26 will result in low pressure in the tubing 21 and through rest of the apparatus to the nozzle 12 as desired. The removal of air from the intermediate portion 72 and the plug opening 77 also causes air to flow from the gage 28 through the tubing 27 (see FIG. 1), the port 96, the bore 94, the lower bore portion 36, through the passageways 92 and 90 the bores 86 and the plug opening 77, outwardly through the port 84 as hereinbefore indicated to operate the pressure gage 28. With the flow of air outward from the pump 26 and with the valve 18 set for a desired rate of air flow, the pressure within the line 24 and consequently within the body 30 of the regulator, including chambers 68 and 37, will become lower and lower since the pump 26 is desirably sized to provide more than the desired amount of flow through the nozzle 12 to allow for adjustment of that flow to provide isokinetic sampling as above described.

With the pump 26 operating to remove more air from the regulator body 30 than is allowed by valve 18 to flow inward from the nozzle 12 to the tubing 21, the pressure in the body 30 becomes low enough to bias the diaphragm 46 downwardly by overcoming the upward bias of the spring 38 so that the ball valve 50 is withdrawn from the seat 65 at the inner end of the passageway 66. It is of course to be realized that the diaphragm 46 is pushed downwardly by the atmospheric air pressure at all times present in the chamber 58 completely covering the top of the diaphragm 46.

When the ball valve 50 is moved downwardly atmospheric air entering through the filter 64 by way of passageway 62 passes through the passageways 66 and 67 into the upper portion of the chamber 68. Atmospheric pressure in chamber 68, with the lower pressure in chamber portions below poppet 80, biases the poppet 80 downwardly until the poppet surface 81 comes in contact with the O ring 82 in the upper end of the opening 77 in the plug element 76 and communication between the port 84 and the port 88 is interrupted, thus preventing air flow from the port 88 by way of the plug opening 77 to the port 84.

Such interruption of communication takes place at a preselected pressure determined by the setting of the adjusting screw 40 increasing or decreasing the upward bias of spring 38 against the diaphragm 46. With air continuing to flow into port 88 by way of tubing 21 the pressure within the body 30 of the regulator 22, including chamber 37, will increase with a consequent increase of the force on the bottom of the diaphragm 46 resulting in upward biasing of valve 50 into sealing contact with the seat 65 at the inner end of passageway 66. When valve 50 has been seated, the communication between the atmosphere and chamber 68 is interrupted and slight leakage around the poppet 80 into the port 84 under vacuum from the pump 26 will cause the pressure within the chamber 68 on the upper side of the poppet 80 to be reduced sufficiently so that the spring 78 will raise the poppet 80 and interrupt the seating of the surface 81 of poppet 68 on the O-ring 82. Thus, communication from the pump 26 through the tubing 24 by way of port 84 is again established with air being removed from the nozzle 12 through the sampling train as desired.

The above described operation will continue with the gage 28 always indicating the existing pressure in the apparatus and the pressure on the dry gas meter 20 being held at a relatively constant figure (plus or minus .05 inches of mercury pressure over a range of 8 to 18 inches of mercury) so that the isokinetic sampling may be accomplished with a minimum of adjustment of the valve 18 and the calculations of the rate of flow will be simplified since the volume of gas as measured by the meter 20 will always be at a substantially constant pressure and no pressure difference factor be needed in the calculations.

Under certain conditions such as tubing 27 being of excessive length it may be desirable to connect the diaphragm chamber 37 directly to the point at which pressure control is desired. In such a case passageway 92 is blocked and port 96, by way of a tee in tubing 27, is connected directly to the gas meter 20 to sense pressure variations within the gas meter more immediately than with the earlier described connections.

A preferred embodiment of the sampling train and pressure regulator of this invention having been hereinabove described it is to be realized that this is only a preferred embodiment and other embodiments applying the principles of this invention are envisioned and possible. It is therefore respectfully requested that this invention be interpreted as broadly as possible limited only by the appended claims.

What is claimed is:

1. A method of isokinetic sampling of a flowing stream of particulate bearing gases comprising the steps of; applying a vacuum to a sampling train communicating with such a stream; measuring the volume rate of gas flow from such a stream through said train; continuously controlling the vacuum pressure of the gas flowing through said train to provide a constant internal vacuum pressure within said train; and said controlling of vacuum pressure is in response to sensing the pressure difference between the gas pressure within the sampling train and the ambient air pressure.

2. A method of isokinetic sampling as set forth in claim 1 comprising the additional step of filtering said gas flow before said measuring of the rate of gas flow.

3. The method of isokinetic sampling as set forth in claim 1 comprising the additional step of condensing the moisture from said gas flow and setting said moisture condensed from said gas flow before said measuring of the rate of gas flow.

4. A method of isokinetic sampling as set forth in claim 1 wherein said sensed difference in pressures is used to open a vacuum control valve in said sampling train when said difference in pressures becomes less than a selected value.

5. A method of isokinetic sampling as set forth in claim 4 wherein said vacuum control valve is closed by applied atmospheric pressure.

6. A method of isokinetic sampling as set forth in claim 5 wherein said applied pressure is provided by a diaphragm operated valve opened by ambient air at atmospheric pressure on one side of a diaphragm working against spring force and vacuum pressure on the other side of said diaphragm.

7. A method of isokinetic sampling as set forth in claim 6 wherein said gas pressure within said train is sensed by direct communication of said diaphragm with said gas flow at the point of measuring said rate of flow.

8. A method of isokinetic sampling as set forth in claim 7 including the additional step of continuously displaying the amount of vacuum pressure as measured in the vicinity of said diaphragm.

9. A method of isokinetic sampling as set forth in claim 1 wherein said applying of vacuum is capable of producing a rate of flow greater than the desired volume rate of flow of such stream through said train.

* * * * *

UNITED STATES PATENT OFFICE
CERTIFICATE OF CORRECTION

PATENT NO. : 3,965,747
DATED : June 29, 1976
INVENTOR(S) : Richard E. McCorkle

It is certified that error appears in the above-identified patent and that said Letters Patent are hereby corrected as shown below:

Claim 3, line 3, delete "setting" and insert -- settling --.

Signed and Sealed this

Fourteenth Day of September 1976

[SEAL]

Attest:

RUTH C. MASON
Attesting Officer

C. MARSHALL DANN
Commissioner of Patents and Trademarks